United States Patent [19]

Groth et al.

[11] Patent Number: 5,670,450
[45] Date of Patent: Sep. 23, 1997

[54] COMPOSITION AND METHOD OF USING FUNGICIDES FOR INHIBITING INDUCED PHYTOTOXICITY IN RICE FROM HALOGENATED AROMATIC HERBICIDES

[75] Inventors: Donald E. Groth, Rayne; Dearl E. Sanders, Slaughter, both of La.

[73] Assignee: Board of Supervisors of Louisiana State University and Agricultural and Mechanical College, Baton Rouge, La.

[21] Appl. No.: 778,028

[22] Filed: Jan. 2, 1997

[51] Int. Cl.⁶ .......................... A01N 25/32; A01N 43/50
[52] U.S. Cl. .............................. 504/103; 504/107
[58] Field of Search ........................ 504/103, 107

[56] References Cited

U.S. PATENT DOCUMENTS 4,749,406 6/1988 Martin .......................... 71/94

FOREIGN PATENT DOCUMENTS 59-204103 11/1984 Japan .

OTHER PUBLICATIONS

Phatak et al., "Growth Regulators, Fungicides, and other Agrochemicals as Herbicide Safeners," pp. 299–315 in K. Hatzios et al. (eds.), *Crop Safeners for Herbicides* (1989).

M. Ogawa et al., "Effects of 3–Hydroxy–5–methylisoxazole on the Reduction of Herbicide Injury to Rice Seedlings," pp. 303–306 in *Proc. Asian–Pac. Weed Sci. Soc. Conf.*, 5th (1975).

S. Aust, "Degradation of Environmental Pollutants by *Phanerochaete chrysosporium*," Microb. Ecol., vol. 20, pp. 197–209 (1990).

Rice Production Handbook, Louisiana State University Agricultural Center (1987).

R. Portier, "Applications of Adapted Microorganisms for Site Remediation of Contaminated Soil and Ground Water," pp. 247–259 in A. Martin (ed.), *Biological Degradation of Wastes* (1991).

*Primary Examiner*—S. Mark Clardy
*Attorney, Agent, or Firm*—John H. Runnels

[57] ABSTRACT

A previously unsuspected cause of herbicide-induced phytotoxicity in rice is disclosed, as is a successful treatment for the problem. Fungi are responsible for dehalogenating halogenated aromatic herbicides. The dehalogenated aromatic compounds then cause serious injury to growing rice plants. The problem has been overcome by treating the herbicide with a fungicide. When fungal metabolism of the herbicide is thus inhibited, the herbicide is not dehalogenated, and the herbicide does not injure rice plants. In a preferred embodiment, the fungicide iprodione was impregnated onto the herbicide thiobencarb, greatly reducing the induced phytotoxicity of the herbicide thiobencarb, without substantially affecting the desired herbicidal activity of thiobencarb.

28 Claims, No Drawings

COMPOSITION AND METHOD OF USING FUNGICIDES FOR INHIBITING INDUCED PHYTOTOXICITY IN RICE FROM HALOGENATED AROMATIC HERBICIDES

The benefit of the Jan. 11, 1996 filing date of the provisional application which was a conversion of nonprovisional application 08/584,526, is claimed under 35 U.S.C. §119 (e).

This invention pertains to decreasing the phytotoxicity to rice plants that can be induced in certain halogenated aromatic herbicides.

Certain halogenated aromatic compounds, particularly certain chlorinated aromatic compounds such as thiobencarb, are commonly used as herbicides to control unwanted plant species in rice fields. These herbicides do not ordinarily injure rice plants (*Oryza saliva L.*). Sometimes, however, an induced phytotoxicity causes these herbicides to injure growing rice plants severely. Despite significant research efforts, the cause of this phenomenon had not previously been understood.

The induced herbicide toxicity to rice has been observed in Japan at least since the mid-1970's, and in the southern United States at least since 1991. To the inventors' knowledge, no prior method of inhibiting this induced phytotoxicity has exhibited much success.

Injured rice plants from commercial fields in south Louisiana were first brought to the inventors' attention in 1991. Injured young plants exhibited stunting, excessive tillering, crooked ("fishhook") tillers, and an overall brittleness. The injured rice plants occurred in commercial fields in irregularly-shaped areas ranging from about 0.01 ha to about 0.1 ha. A total of about 25 ha of Louisiana rice fields was affected in 1991; no cause was determined.

In 1992 rice plants from Louisiana fields exhibiting the same symptoms were again brought to the attention of the inventors and others. In 1992 approximately 2500 ha of commercial rice plantings suffered from the induced phytotoxicity symptoms. Comparable figures for more recent growing seasons are not currently available, but anecdotal evidence strongly suggests that the incidence of induced rice phytotoxicity in Louisiana is increasing. Similar induced rice phytotoxicity symptoms have been reported in South Texas.

The weed red rice is often inhibited by the flooding of rice fields; however, fields that were flooded often exhibited an increase in the induced mortality, because it was more difficult for weakened rice plants to emerge from the water.

The symptoms were similar to those known to be caused by excessive application of the herbicide molinate. Soil samples from five affected Louisiana fields were therefore analyzed for the presence of molinate, but none was detected.

A survey of the farmers found that about ninety percent of the fields in question had been water-seeded in conjunction with one or more of the following herbicides: thiobencarb (Bolero™) (S-4-chlorobenzyl diethylthiocarbamate); quinclorac (Facet™) (3,7-dichloro-8-quinolinecarboxylic acid); propanil (N-(3,4-dichlorophenyl)propanamide); 2,4-D (2,4-dichlorophenoxyacetic acid); and triclopyr (Grandstand™) ([(3,5,6-trichloro-2-pyridinyl)oxy]acetic acid). The active ingredient of each of these herbicides is a halogenated aromatic compound. About 65% of the affected fields had been treated with thiobencarb. Thiobencarb is sold by Valent under the name Bolero™.

A halogenated aromatic herbicide that is commonly used in rice fields in Japan, but that currently is not frequently used in the United States for this purpose, is oxadiazon, sold by Rhône Poulenc under the name Ronstar™, 3 -[2,4-dichloro-5-(1 -methylethoxy)phenyl]-5-(1,1 -dimethylethyl) -1,3,4-oxadiazol-2(3H)-one.

A similar problem has been reported for Japanese rice fields since the mid-1970's, where the problem has also been associated with thiobencarb. The cause of the Japanese rice problem had previously been identified as the dechlorination of thiobencarb by an unidentified facultative anaerobic bacterium. It had previously been reported that the problem in Japan could be overcome by reducing the rate of application of the active ingredient, and by adding an antibacterial agent to the herbicide. T. Shinohara, Kumiai Chemical Industry Co. Ltd. (Japan) (personal communication, 1993).

The inventors obtained a sample of the antibacterial agent that has been used in conjunction with thiobencarb in Japan. (Although the identity of this agent was unspecified by the manufacturer, it was specifically identified as an antibacterial agent.) The antibacterial agent was applied to thiobencarb in accordance with the instructions supplied by the manufacturer, Kumiai. The treated thiobencarb was used in 1993 in a rice field that had exhibited substantial injury during the 1992 season. Despite the use of the treated thiobencarb, substantial injury and rice mortality were still observed in this field in 1993.

General background on the cultivation of rice may be found in the Rice Production Handbook, Louisiana State University Agricultural Center (1987).

C. Phatak et al., "Growth Regulators, Fungicides, and other Agrochemicals as Herbicide Safeners," pp. 299–315 in K. Hatzios et at. (eds.), *Crop Safeners for Herbicides* (1989) includes a review of the relatively small literature on prior uses of fungicides as herbicide safeners (pp. 302–304).

M. Ogawa et al., "Effects of 3-Hydroxy-5-methylisoxazole on the Reduction of Herbicide Injury to Rice Seedlings," pp. 303–306 in *Proc. Asian-Pac. Weed Sci. Soc. Conf.*, 5th (1975) discloses laboratory experiments on the effect of pretreatment of rice with the fungicide 3-hydroxy-5-methylisoxazole (HMI) against herbicide-induced injury. HMI was applied to soil immediately after sowing rice seeds. Seedlings were transplanted 20 days later, and herbicide was applied 3 days after transplanting. It was reported that pretreatment with HMI reduced the phytotoxic effects of the herbicides simetryne, nitrofen, CNP, propanil, and swep-MCPA. HMI pretreatment conferred no protective effects, however, against the herbicide combinations benthiocarb·simetryne or benthiocarb·CNP 18 days after treatment. (Note that "benthiocarb" is an earlier name for "thiobencarb.") Ogawa et al. reported that herbicidal injury was not reduced when HMI was applied simultaneously with herbicide, but only when HMI was applied as a pre-treatment to rice seeds. The authors suggested that the reduction of herbicidal injury might be due to increased seedling vigor induced by HMI. On addition to its fungicidal properties, HMI is also known to be a growth stimulant.)

The white rot fungus *Phanerochaete chrysosporium* is available commercially, and has been suggested for use in the bioremediation of environmental pollutants, including DDT, TCDD, benzo(a)pyrene, Lindane, and certain PCB congeners. See S. Aust, "Degradation of Environmental Pollutants by *Phanerochaete chrysosporium*," Microb. Ecol., vol. 20, pp. 197–209 (1990).

R. Portier, "Applications of Adapted Microorganisms for Site Remediation of Contaminated Soil and Ground Water," pp. 247–259 in A. Martin (ed.), *Biological Degradation of Wastes* (1991) discloses the use of fungi in the bioremediation of pentachlorophenol-contaminated creosote waste soils.

To the inventors' knowledge, no prior treatment of halogenated aromatic herbicides has successfully addressed the induced rice phytotoxicity problem—at least not in the United States. It is possible that the treatment that has been used in Japan does not work in the United States because the sources of the apparently similar problems are different in the two countries. At least in the United States, to the inventors' knowledge the source of the induced phytotoxicity has not previously been correctly identified; nor has a successful solution to the problem previously been found.

We have discovered the previously unsuspected cause of herbicide-induced phytotoxicity in rice, and have also discovered a successful treatment for the problem. We have discovered that fungi are responsible for dehalogenating the halogenated aromatic herbicides that are used in rice fields. The dehalogenated aromatic compounds can then cause serious injury to growing rice plants. The problem has been overcome by directly treating the herbicide with a fungicide. When fungal metabolism of the herbicide is thus inhibited, the herbicide is not dehalogenated, and the herbicide does not injure rice plants. In a preferred embodiment, the fungicide iprodione (3-(3,5-dichlorophenyl)-N-(1-methylethyl)-2,4-dioxo-1-imidazolidinecarboxamide) was impregnated onto the herbicide thiobencarb, greatly reducing the induced phytotoxicity of the herbicide thiobencarb, without substantially affecting the desired herbicidal activity of thiobencarb.

Greenhouse Studies

EXAMPLES 1–8

The white mold fungus *Phanerochaete chrysosporium* was inoculated into sterile soil in pots, some with and some without thiobencarb. Rice seedlings at the four-leaf stage were transplanted into the soil, and the pots were flooded. The plants were monitored for phytotoxicity.

Plants in the soil inoculated with *P. chrysosporium* and thiobencarb exhibited phytotoxicity symptoms similar to those seen in the field. Subsequent chemical analysis found that dechlorothibencarb was present in the soil.

Plants in soil inoculated with the fungus, but lacking thiobencarb, grew normally. The results are shown in Table I. In Table I (and all other tables), mean values in a particular column that are followed by the same letter did not differ significantly from one another (at the P=0.05 level, as determined by Duncan's multiple regression test).

TABLE I

| | Treatment | Degree of Injury (0–9, 9 = dead) |
|---|---|---|
| 1. | no treatment, infested soil | 0.0 c |
| 2. | no treatment, steamed soil | 0.0 c |
| 3. | thiobencarb, infested soil | 5.0 a |
| 4. | thiobencarb, steamed soil | 0.0 c |
| 5. | triclopyr, infested soil | 2.7 b |
| 6. | triclopyr, steamed soil | 0.0 c |
| 7. | quinclorac, infested soil | 3.3 b |
| 8. | quinclorac, steamed soil | 0.0 c |
| | LSD (0.05) (least significant difference, P = 0.05) | 1.6 |
| | CV (coefficient of variation) | 68.3 |

EXAMPLE 9

Four-leaf rice seedlings were transplanted into pots containing unsterilized soil taken from a field where induced phytotoxicity symptoms had been observed. This soil was treated with thiobencarb. When the plants began exhibiting symptoms, a soil sample was collected from underneath the plant, and microorganisms from the soil were isolated by the dilution plate method. Cultures of the isolated microorganisms were then tested for their ability to dechlorinate thiobencarb in a bioassay in sterile soil. A naturally-occurring fungus having the ability to dechlorinate thiobencarb was isolated, tentatively identified as *Trichoderma* sp. This fungus (and perhaps other fungi as well) are believed to be responsible for herbicide-induced phytotoxicity in rice.

EXAMPLES 10–13

Soil from a field exhibiting thiobencarb-induced delayed phytotoxicity was placed in 18 cm diameter plastic pots. Herbicide and fungicide were applied to the soil in liquid form, and the soil was flooded. The treatments were as follows: (10) an unsprayed check as a control, (11) thiobencarb 3 EC at 4.6 kg/ha a.i. (active ingredient), (12) a tank mixture of two fungicides, benomyl and iprodione, at 1.12 kg/ha a.i. each (benomyl=methyl-1 -(butylcarbamoyl) benzimidazol-2-ylcarbamate), and (13) a tank mixture of thiobencarb, benomyl, and iprodione at the same rates used in Examples (11) and (12). Two four-leaf rice seedlings, cultivar Mars, were transplanted into each pot. The experiment was conducted as a randomized complete block design, with three replications of each treatment. The plants were monitored for symptoms of delayed phytotoxicity. The results are shown in Table II. Iprodione is a fungicide manufactured by Rhône Poulenc, and sold under the name Rovral™. Benomyl is a fungicide manufactured by E.I. DuPont de Nemours and Company, and sold under the name Benlate™.

TABLE II

| | Treatment | Degree of Injury (0–9, 9 – dead) | Plant Height (cm) |
|---|---|---|---|
| 10. | unsprayed check | 0.0 b | 93 c |
| 11. | thiobencarb | 5.7 a | 40 e |
| 12. | benomyl + iprodione | 0.0 b | 65 d |
| 13. | thiobencarb + benomyl + iprodione | 0.0 b | 67 d |
| | LSD (0.05) | 1.2 | 8.5 |
| | CV | 40.8 | 6.44 |

Severe injury was seen within 30 days after treatment for the plants treated with thiobencarb alone. Phytotoxicity symptoms were not seen on the plants treated with the mixture of thiobencarb, benomyl, and iprodione. Some phytotoxicity was noted on the plants treated with benomyl and iprodione, in the form of small defuse brown spots on leaves and some stunted growth; this phytotoxicity was attributed to the high rate of fungicide application used in this treatment.

EXAMPLES 14–22

These treatments were similar to those used in Examples 10–13 above, except as noted. Where herbicide and fungicide treatments were both used, the treatments were applied sequentially, rather than as the mixture of treatments 12 and 13 above. Except for the treated rice seeds used in Examples 19–21, all treatments were applied to the soil in liquid form. The treatments were as follows: (14) unsprayed check as a control, (15) thiobencarb at 4.5 kg/ha a.i., (16) thiobencarb at 4.5 kg/ha a.i. and benomyl at 0.28 kg/ha a.i., (17) thiobencarb at 4.5 kg/ha a.i. and iprodione at 0.28 kg/ha a.i., (18) thiobencarb at 4.5 kg/ha a.i. and metalaxyl at 0.28 kg/ha a.i. (metalaxyl=N-(2,6-dimethylphenyl)-N-(methoxyacetyl) -(D,L)-alanine methyl ester), (19) thiobencarb at 4.5 kg/ha a.i., with one cupric hydroxide-treated rice seed (0.07 kg a.i. per 45.4 kg seed) placed 1 cm deep at the base of each plant, (20) one mancozeb-treated rice seed (0.08 k a.i. per 45.4 kg seed) placed 1 cm deep at the base of each plant (mancozeb is a coordination product of the zinc ion with manganese ethylene bisdithiocarbamate), (21) thiobencarb at 4.5 kg/ha a.i., with 4–6 mancozeb-treated rice seeds (0.08 k a.i. per 45.4 kg seed) placed on the soil surface near the plant, and (22) thiobencarb at 4.5 kg/ha a.i., benomyl at 0.28 kg/ha a.i., and iprodione at 0.28 kg/ha a.i. Rice injury ratings were assessed thirty days after planting. The results are shown in Table III.

TABLE III

| | Treatment | Degree of Injury (0–9, 9 = dead) |
|---|---|---|
| 14. | unsprayed check | 0.0 c |
| 15. | thiobencarb | 6.0 ab |
| 16. | thiobencarb + benomyl | 7.3 a |
| 17. | thiobencarb + iprodione | 7.3 a |
| 18. | thiobencarb + metalaxyl | 4.3 b |
| 19. | thiobencarb + cupric hydroxide-treated seed | 3.7 b |
| 20. | thiobencarb + mancozeb-treated seed | 7.0 a |
| 21. | thiobencarb + 4–6 mancozeb treated seeds | 4.3 b |
| 22. | thiobencarb + benomyl + iprodione | 0.0 c |
| | LSD (0.05) | 2.5 |
| | CV | 29.1 |

Again, severe phytotoxicity symptoms developed on plants treated with thiobencarb only. However, none of the plants would have been commercially acceptable except for the untreated plants, and the thiobencarb+benomyl+iprodione treated plants.

Field Studies

EXAMPLES 23–28

Different treatments were tested in two field studies in 1995; the first field study encompassed Examples 23–28, and the second encompassed Examples 29–31. The field studies were conducted in a field at the Louisiana Agricultural Experiment Station's Rice Research Station in Crowley, La. The field used had exhibited thiobencarb-induced phytotoxicity in both 1993 and 1994 prior to use in the 1995 study. This field also had a naturally-occurring red rice weed population. (Red rice is a persistent weed problem in the cultivation of rice; red rice belongs to the same species as commercial varieties of rice, but has inferior qualities.) The field was flooded to a depth of 15 cm. Soil was prepared for planting by cultivation in water using standard methods. Galvanized steel cylindrical rings with a height of 30 cm and a diameter of 91.5 cm were pressed securely into the impermeable subsoil immediately following soil preparation.

As the results below indicate, an improved method of application of the fungicide-herbicide combination greatly improved the treatment as compared to the liquid-based applications used in the greenhouse studies reported above. In particular, it was found highly advantageous to impregnate the fungicide onto granules containing the herbicide. The impregnated fungicide significantly reduced fungal metabolism of the herbicide.

In the first field study, clay granules were impregnated with thiobencarb, iprodione, and/or benomyl as indicated forty days prior to use. In all cases, the clay granules used were Agsorb™ 16/30 LVM-MS granules from Oil-Dri Corporation of America (Chicago, Ill.). The typical analysis provided by the manufacturer for the untreated clay granules was as follows: mineral classification, montmorillonite; volatile classification, LVM; density, 32.0–37.0 lb./cu. ft.; pH 3.0–7.0; free water at time of manufacture, 0%; hardness (resistance to attrition), 75.0–90.0%; liquid holding capacity, 31.0–35.0%; particle count, 1500–2500 per pound; sieve analysis, >90% at 16–30; color, brown/tan. The typical chemical analysis provided by the manufacturer was as follows (expressed as weight percentages): $SiO_2$, 76.72; $Al_2O_3$, 11.28; CaO, 0.63; MgO, 2.04; $Na_2O$, 0.10; $K_2O$, 1.26; $Fe_2O_3$, 6.51; MnO, 0.01; $P_2O_5$, 0.11; $TiO_2$, 0.52; FeO, 0.82; LOI, 2.20. Where clay granules impregnated with thiobencarb were used, those granules were received from the manufacturer (Valent) already impregnated with thiobencarb as standard Bolero 10 G granules (10% active ingredient by weight), and were used as received—except where further impregnation with a fungicide is indicated below.

Other inert, preferably dry carriers could be used in place of clay granules. Carriers that are commonly used for the application of agricultural chemicals include clay granules, sand, and corn-cob grit.

Blank or thiobencarb-impregnated clay granules of otherwise identical specification were treated with fungicide as follows. The granules were divided into 0.454 kg portions. A 0.454 kg portion was placed into a Gilson rotating tumbler at 40 rpm. Fresh benomyl (DuPont), 11.35 gram, was suspended in 20 ml water, which was then aspirated evenly onto the rotating granules with a hand aspirator. The tumbler was allowed to run for five minutes following this application. The granules were removed and stored in sealed polyvinyl bags at 22° C. for forty days, until used.

A separate 0.454 kg portion of blank or thiobencarb-impregnated granules was placed into a Gilson rotating tumbler at 40 rpm. Fresh iprodione (Rhône Poulenc), 11.6 ml, was suspended in 20 ml water, which was then aspirated evenly onto the rotating granules with a hand aspirator. The tumbler was allowed to run for five minutes following this application. The granules were removed and stored in sealed polyvinyl bags at 22° C. for forty days, until used.

The clay granules were applied at a total rate of 44.8 kg/ha at the following treatments and application rates of active ingredient: (23) thiobencarb at 4.6 kg/ha a.i. and benomyl at 0.288 kg/ha a.i., (24) thiobencarb at 4.6 kg/ha a.i. and iprodione at 0.288 kg/ha a.i., (25) benomyl at 0.288 kg/ha a.i., (26) iprodione at 0.288 kg/ha a.i., (27) thiobencarb at 4.6 kg/ha a.i., and (28) control (untreated clay granules). In each case, the granules were spread by hand into the flooded rings before seeding; the granules were denser than water and sank to the bottom. The rings were left undisturbed for 48 hours. Pre-sprouted rice seed, cultivar Mars, was then evenly placed inside the flooded rings at a rate of 112 kg/ha. The rings were left undisturbed for four hours while the water in the surrounding field was drained. Then the rings were carefully raised to allow the water within to drain, without disturbing the seed. The rings were replaced after 24 hours, and were flooded to a depth of 5 cm. The tests included three replications of each treatment in a complete randomized block design. Injury ratings were assessed 7 days and 30 days after planting. Red rice levels were assessed 30 days after planting. Results are presented in Table IV.

TABLE IV

| Treatment of Clay Granules | Percentage of plants lost, Mars Cultivar, 7 days after planting | Percentage of plants lost, Mars Cultivar, 30 days after planting | Percentage of plants lost, Red Rice, 30 days after planting |
| --- | --- | --- | --- |
| 23. thiobencarb + benomyl | 28.3 b | 91.3 b | 78.3 b |
| 24. thiobencarb + iprodione | 1.7 c | 0.0 c | 80.0 b |
| 25. benomyl | 3.3 c | 0.0 c | 0.0 b |
| 26. iprodione | 0.0 c | 0.0 c | 0.0 c |
| 27. thiobencarb | 94.7 a | 99.7 c | 99.7 a |
| 28. untreated granules | 1.7 c | 0.0 c | 0.0 c |
| LSD (0.05) | 5.3 | 5.3 | 4.1 |
| CV | 13.4 | 4.1 | 5.2 |

By seven days after planting about 95% of the Mars cultivars were lost where thiobencarb was applied alone, compared to only about a 2% loss for thiobencarb plus iprodione, and about a 2% loss for the control. Little change occurred between 7 days and 30 days for these two treatments. By contrast, thiobencarb plus benomyl plots exhibited only about a 28% loss at 7 days, but the loss had climbed to about 91% after 30 days. The iprodione-alone, benomyl-alone, and untreated plots showed little or no injury to the rice plants. The reduction in the figures in Table IV in some rows (e.g., benomyl) from the "7-day" column to the "30-day" column reflects the fact that some rice plants emerged after the first 7 days.

Note the substantial improvement for the preferred thiobencarb+iprodione treatment in Table IV as compared to Table III. This improvement was attributed to the improved method of application used in these trials, i.e., impregnating the fungicide onto the herbicide.

The control of red rice depended on whether the thiobencarb was treated with fungicide. Treatment with thiobencarb alone in this field resulted in nearly complete red rice mortality. By contrast, treatment with thiobencarb and fungicide resulted in about 80% control of red rice, a figure that is comparable to the degree of red rice control that has been previously reported for thiobencarb in fields where thiobencarb-induced phytotoxicity of commercial rice cultivars had not been observed. See J. Baker et al., "Chemical Control of Red Rice in Rice," 77th Ann. Prog. Rept.—Rice Res. Sta., La. Ag. Exp. Sta., pp. 177–182 (1985).

EXAMPLES 29–31

The second field study was similar to the first, except as noted. All rings were treated with thiobencarb-impregnated granules, applied at an effective rate of 4.6 kg/ha a.i. of thiobencarb. Fungicide was applied to seeds of cultivar Mars (rather than to the clay granules). The treatments were as follows: (29) mancozeb at 0.09 k a.i. per 45.4 kg seed, (30) cupric hydroxide at 0.07 a.i. per 45.4 kg of seed, and (31) no treatment applied to seed as comparison. The tests included three replications of each treatment in a complete randomized block design. Rice injury ratings were assessed thirty days after planting. Results are presented in Table V.

TABLE V

| Treatment | Percentage of plants lost, Mars Cultivar, 30 days after planting |
| --- | --- |
| 29. mancozeb | 88.3 a |
| 30. cupric hydroxide | 65.0 b |
| 31. control | 98.3 c |
| LSD (0.05) | 3.8 |
| CV | 10.34 |

Mancozeb-treated seed and cupric hydroxide-treated seed resulted in about 12% and 35% survival, respectively, for rice plants after 30 days, compared to about 2% for the untreated control. While this level of injury control is commercially unacceptable, it does illustrate that fungicides enhanced the survival of rice plants otherwise subject to thiobencarb-induced phytotoxicity.

These results show that fungicides such as iprodione and benomyl can reduce the phytotoxicity that can otherwise result from dehalogenation of halogenated aromatic herbicides such as thiobencarb, benomyl to a lesser degree than iprodione. It is preferred that the fungicide be impregnated onto the carrier for the herbicide, as this treatment appears to maximize the antifungal activity; enhanced antifungal activity, in turn, reduces the otherwise phytotoxic effects of fungal dehalogenation of the herbicide.

This invention will work with any halogenated aromatic herbicide used in rice fields where fungally-induced phytotoxicity to rice plants is identified. Such herbicides may include not only those discussed previously, but the following herbicides as well: anilofos, sold by Agrevo under the name Arozin™, S-[2-[(4-chlorophenyl)(1-methylethyl)amino]-2-oxoethyl]O,O-dimethylphosphorodithioate; MCPA-thioethyl, sold by Hokko Chemical under the name Herbit™, S-ethyl (4-chloro-2-methylphenoxy)ethanethioate; pyrazoxyfen, sold by ISK Agro under the name Paicer™, 2-[[4-(2,4-dichlorobenzoyl)-1,3-dimethyl-1H-pyrazol-5-yl]oxy]-1-phenylethanone;clomeprop, sold by Mitsubishi Kagaku under the name Yukahope™, (±)-2-(2,4-dichloro-3-methylphenoxy-N-phenylpropanamide; chlornitrofen, sold by Mitsui Toatsu under the name MO™, 1,3,5-trichloro-2(4-nitrophenoxy)benzene; bifenox, sold by Rhône Poulenc under the name Modown™, methyl 5-(2,4-dichlorophenoxy)-2-nitrobenzoate; or pyrazolynate, sold by Sankyo under the name Sanbird™, (2,4-dichlorophenyl)[1,3-dimethyl-5-[[(4-ethylphenyl) sulfonyl]oxy]-1H-pyrazol-4-yl]methanone.

We claim:

1. A composition of matter useful for controlling weeds in a rice field without inducing substantial phytotoxicity in rice plants, said composition comprising a mixture of a halogenated aromatic herbicide suitable for use in a rice field, and a fungicide, wherein the concentration of said fungicide is sufficient to inhibit fungal dehalogenation of said halogenated aromatic herbicide.

2. A composition as recited in claim 1, wherein said herbicide and said fungicide are impregnated onto an inert carrier.

3. A composition as recited in claim 1, wherein said halogenated aromatic herbicide comprises thiobencarb, and wherein said fungicide comprises iprodione.

4. A composition as recited in claim 3, wherein said thiobencarb and said iprodione are impregnated onto an inert carrier.

5. A composition as recited in claim 1, wherein said halogenated aromatic herbicide comprises quinclorac, and wherein said fungicide comprises iprodione.

6. A composition as recited in claim 5, wherein said quinclorac and said iprodione are impregnated onto an inert carrier.

7. A composition as recited in claim 1, wherein said halogenated aromatic herbicide comprises triclopyr, and wherein said fungicide comprises iprodione.

8. A composition as recited in claim 7, wherein said triclopyr and said iprodione are impregnated onto an inert carrier.

9. A composition as recited in claim 1, wherein said halogenated aromatic herbicide comprises 2,4-D, and wherein said fungicide comprises iprodione.

10. A composition as recited in claim 9, wherein said 2,4-D and said iprodione are impregnated onto an inert carrier.

11. A composition as recited in claim 1, wherein said halogenated aromatic herbicide comprises propanil, and wherein said fungicide comprises iprodione.

12. A composition as recited in claim 11, wherein said propanil and said iprodione are impregnated onto an inert carrier.

13. A composition as recited in claim 1, wherein said halogenated aromatic herbicide comprises oxadiazon, and wherein said fungicide comprises iprodione.

14. A composition as recited in claim 13, wherein said oxadiazon and said iprodione are impregnated onto an inert carrier.

15. A process for controlling weeds in a rice field without inducing substantial phytotoxicity in rice plants; said process comprising applying to the rice field a composition comprising a mixture of a halogenated aromatic herbicide suitable for use in a rice field, and a fungicide, wherein the concentration of the fungicide is sufficient to inhibit fungal dehalogenation of the halogenated aromatic herbicide.

16. A process as recited in claim 15, wherein the herbicide and the fungicide are impregnated onto an inert carrier.

17. A process as recited in claim 15, wherein the halogenated aromatic herbicide comprises thiobencarb, and wherein the fungicide comprises iprodione.

18. A process as recited in claim 17, wherein the thiobencarb and the iprodione are impregnated onto an inert carrier.

19. A process as recited in claim 15, wherein the halogenated aromatic herbicide comprises quinclorac, and wherein the fungicide comprises iprodione.

20. A process as recited in claim 19, wherein the quinclorac and the iprodione are impregnated onto an inert carrier.

21. A process as recited in claim 15, wherein the halogenated aromatic herbicide comprises triclopyr, and wherein the fungicide comprises iprodione.

22. A process as recited in claim 21, wherein the triclopyr and the iprodione are impregnated onto an inert carrier.

23. A process as recited in claim 15, wherein the halogenated aromatic herbicide comprises 2,4-D, and wherein the fungicide comprises iprodione.

24. A process as recited in claim 23, wherein the triclopyr and the iprodione are impregnated onto an inert carrier.

25. A process as recited in claim 15, wherein the halogenated aromatic herbicide comprises propanil, and wherein the fungicide comprises iprodione.

26. A process as recited in claim 25, wherein the propanil and the iprodione are impregnated onto an inert carrier.

27. A process as recited in claim 15, wherein the halogenated aromatic herbicide comprises oxadiazon, and wherein the fungicide comprises iprodione.

28. A process as recited in claim 27, wherein the oxadiazon and the iprodione are impregnated onto an inert carrier.

* * * * *